US006413553B1

(12) United States Patent
Bandyopadhyay et al.

(10) Patent No.: US 6,413,553 B1
(45) Date of Patent: Jul. 2, 2002

(54) **HERBAL FORMULATION OF A COMBINATION OF *PIPER BETEL* AND *MURRYA KOENIGII* EXTRACTS FOR BLOCKING 5 LIPOXYGENASE ACTIVITY**

(75) Inventors: Santu Bandyopadhyay; Keshab Chandra Roy; Mitali Roy; Bikash Chandra Pal; Ranjan Bhadra; Krishna Das; Samir Bhattacharaya, all of Kolkata (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/925,415

(22) Filed: Aug. 10, 2001

(51) Int. Cl.[7] .............................................. A61K 35/78
(52) U.S. Cl. ....................................... 424/734; 424/725
(58) Field of Search ................................. 424/734, 725

(56) References Cited

FOREIGN PATENT DOCUMENTS

JP          09278666       * 10/1997
JP          11130685       * 5/1999

OTHER PUBLICATIONS

Vaijayanthimala et al., Phytotherapy Research, May 2000, 14 (3), 207–9.*

* cited by examiner

*Primary Examiner*—David M. Naff
*Assistant Examiner*—Mike Meller
(74) *Attorney, Agent, or Firm*—Foley & Lardner

(57) ABSTRACT

A pharmaceutical formulation is provided which is useful as a leukotrine synthesis and IL4 inhibitor and as a Th1 immunomodulator. The formulation comprises an effective amount of a combination of extracts and lyophilized extracts of *Piper betel* and *Murrya koeniggi*. The formulation can be formulated with pharmaceutically acceptable carriers. The formulation can be used in a method of treating humans for respiratory conditions.

20 Claims, 1 Drawing Sheet

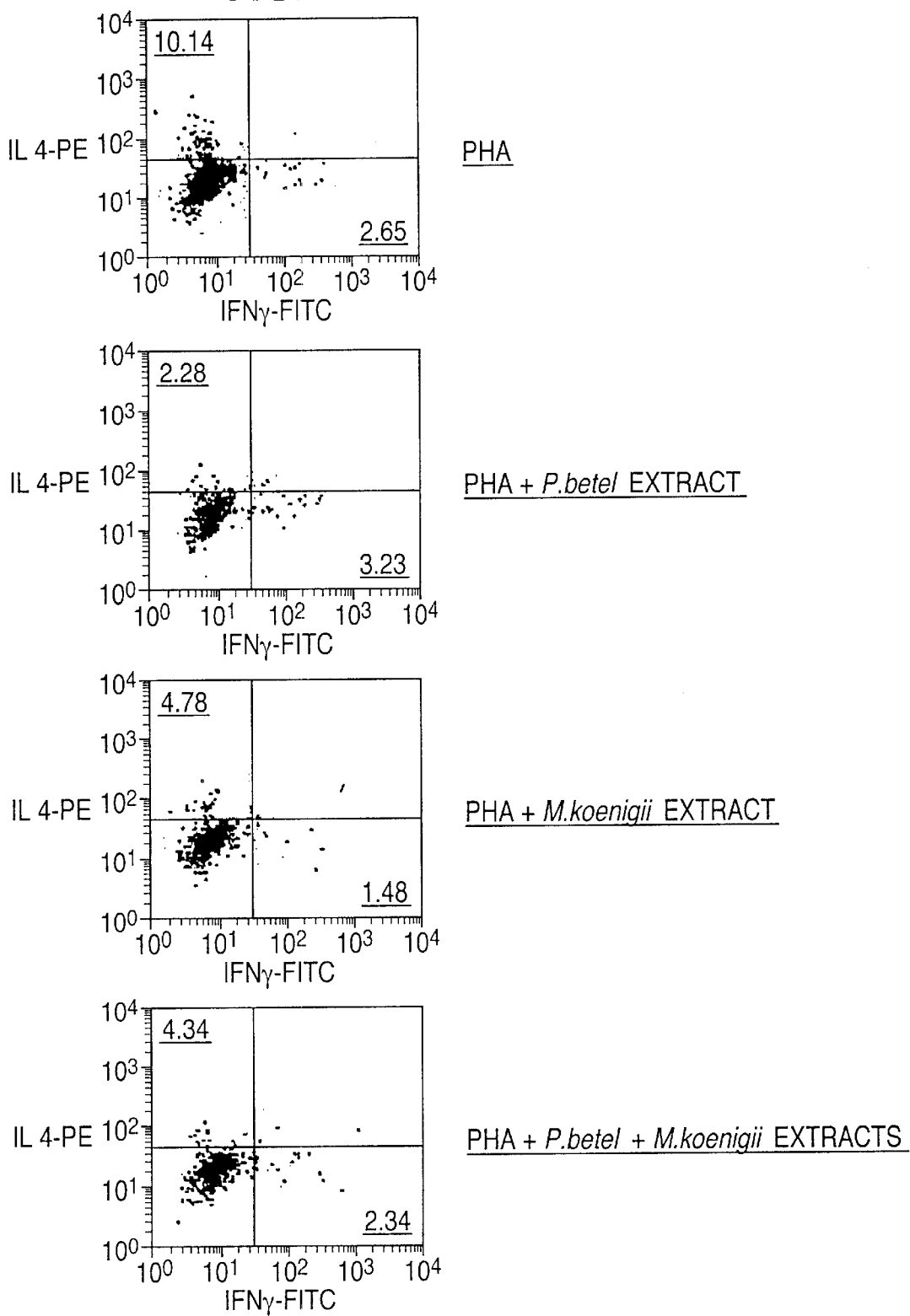

HERBAL FORMULATION OF A COMBINATION OF *PIPER BETEL* AND *MURRYA KOENIGII* EXTRACTS FOR BLOCKING 5 LIPOXYGENASE ACTIVITY

FIELD OF THE INVENTION

This invention relates to an herbal formulation useful for blocking of 5 lipoxygenase activity leading to the inhibition of leukotrine synthesis, suppression of IL4 production and enhancement of IFN gamma release. More particularly this invention describes the process for the preparation of extracts from the leaves or any other plant parts of plants *M. koenigii* and *P. betel* and their selective blending to evaluate biological response in order to establish their role for the treatment and remedy of bronchial respiratory troubles.

BACKGROUND AND PRIOR ART REFERENCES

Respiratory problems consist of mild to extremely severe trouble of breathing along with the other discomforts such as wheezing, coughing, chest tightness and the like. In spite of precautionary measure, public awareness campaign and monitoring system, population having respiratory trouble is on the rise all over the world. This is more true in western advanced countries, specially among the children. With *M. koenigii* leaf preparation, the relief and possible cure of asthma has been demonstrated in a large number of cases (Unpublished PCT Patent application PCT/IN/00102). Two-prong strategy was adapted in the present invention. The respiratory disease is the result of pathophysiological symptoms arising out of aberration of immune system. The immediate symptom includes bronchial constriction, inflammation of respiratory tract and closing of air way by mucus secretion. The symptomatic drugs provide relief by temporary relaxation of the distressed symptoms.

This is to state that the *Murrya koenigii* extract combined with extract obtained from piper betel has shown surprising results. According to the earlier filed unpublished PCT patent application, the betel leaf extract showed increase in IFN-γ from Th1 type cells and decrease of IL-4 from Th2 type cells. This clearly is an effective measure in treating asthma as shifting of Th2 type response towards Th1 type will obviously reduce the release of IgE from mast cells which is a major manipulator of asthmatic condition. Hence the applicants earlier finding followed by the filing of PCT patent application PCT/INOO/00127 is in direct consonance with the present filing on combined extracts from any plant parts of *M. koenigii* and *P. betel* as a new medicine for treating atopic Asthma.

The root cause for respiratory problems is not well addressed by the developers of symptomatic drugs. With the advent of current knowledge, it is now well accepted that leukotrienes are found to be the main player in developing symptoms of respiratory problems.

The major symptoms of respiratory problem can be divided into early and late responses. The early response occurs within minutes of allergen exposure and involves primarily mediators such as histamine, leukotrienes and prostaglandin D2. The effects of these mediators result in bronchoconstriction and accumulation of mucus. The late response occurs hours later and involves additional mediators including IL-4, IL-5, IL-6, and TNF-alpha, eosinophils chemotactic factor (ECF) and platelet activating factor (PAF). The overall effect of these mediators is to recruit inflammatory cells including eosinophils and neutrophils. These cells are capable of causing significant tissue injury by releasing toxic enzymes. These events lead to occlusion of bronchial lumen with mucus protein, and cellular debris, thus thickening of basement membrane, fluid build up and hypertrophy of the bronchial smooth muscle. A mucus plug often forms and adheres to the bronchial wall. The mucus plug contains clusters of detached epithelial cells fragments, eosinophils, some neutrophils and spirals of bronchial tissue known as Curschmann's spiral (Immunology, J. Kuby; W.H. Freeman & Co., New York; 3rd edition 1997). In view of the current mechanisms regarding manifestation of bronchial asthma/ bronchial respiratory problems, modem strategy for drug development stressed the following approaches:

These include i) inhibition of leukotriene synthesis via blocking the 5-lipoxygenase-enzyme activity (Leqqis RA et al New England J. Med. 323:,645,1990). The formation of leukotrienes originates from the oxidation of arachidonic acid, hence inhibition of this reaction leads to the inhibition of leukotriene synthesis. Besides, leukotrine receptors antagonists have also been introduced as anti leukotriene therapy for asthma/respiratory problems (Tien F. C., Medical J. Aust. 171: 378,1999). Currently licensed drug zelutin, based on inhibition of arachidonic acid oxidation has already been introduced exclusively in the US market. However, its use is limited by hepatotoxicity. Children below 14 years are not recommended for this drug. Moreover patients taking other drugs need to be surveyed when taking zelutin as anti-asthma drug. More over patients taking other drugs need to be surveyed when taking zelutin, as anti-asthma drug. ii) the neutralization of IgE either by anti-IgE antibody (humanized) or by blocking the high affinity IgE receptor, FcεR-I (Heusser C, Jardiu P. Current Oppinio Immunol., 9: 805.1999). Since suppression of Th2 cytokines leads to decrease in IgE production, additional approach is based on the inhibition of these Th2 cytokine synthesis and enhancement of Th1 cytokine formation (Chung K. F.; Barens P. J. Thorax 54: 825, 1999).

In contrast, *M. koenigii* based anti asthmatic preparation has been tried on children as young as 7 years old and octogenarian as old as 80 years and above without any adverse reaction.

The extract of *M. koenigii* leaf was therefore examined for their potential to inhibit the production of leukotrienes. Additionally, the extract was also examined for shifting of Th2 response towards to Th1 type. Th1 and Th2 response were measured by γ-interferon (Th 1) and IL-4 (Th2) production respectively. *M. koenigii* extract showed inhibition of 5-lipoxygenase mediated arachidonic acid oxidation signifying blockage of leukotriene synthesis and marginal effect on γ-interferon production. Importantly, *M. koenigii* extract drastically reduces IL-4 synthesis. On the other hand, *P. betel* leaf extracts resulted in facilitating of the shift from Th2 type response to Th1 type. In other words, a man having average skill in the art cannot just combine these two to produce inference of the combination of the ingredients. This combination is a novel combination and the combined effects of the combination are surprising and unexpected. Thus, a blend of extracts from these two plants, *M. koenigii* and *P. betel* predominantly inhibited leukotriene synthesis and shifted Th2 response towards Th1 type and therefore is proposed as a unique synergistic formulation for treatment, relief and remedy of bronchial respiratory problems. Thus, the two pronged strategy is the major objective of this new formulation and can be considered as the best modality of treatment for patients suffering from bronchial respiratory problems.

OBJECTS OF THE INVENTION

The main objective of the invention is to provide a new pharmaceutical formulation comprising combination of extracts derived from plant parts leaves of *Murraya koenigii* and *Piper betel* or any of the plant parts thereof.

Another object of the invention is to provide a new pharmaceutical formulation comprising combination of extracts derived from *Murraya koenigii* and *Piper betel* leaves.

Yet another objective of the present invention is to provide a process for the preparation of extract from the leaves or any other plant parts of *M. koenigii* and *P. betel* useful for relief, treatments and remedy of respiratory problem.

Yet another objective of the present invention is to provide a simplified method of extract preparation from leaves or any other plant parts of *M. koenigii* and *P. betel* possessing biological activities relevant to treatment, relief and remedy of respiratory problems.

Yet another objective of the present invention is to provide a simplified fast and inexpensive process for the preparation of combination of extracts possessing biological activities relevant to treatments, relief and remedy of respiratory problems.

Yet another objective of the present invention is to provide a herbal preparation comprising of extracts derived from *M. koenigii* and *P. betel* leaves or extracts obtained from other plant parts of *M. Koenigii* and *P. betel*, wherein the said extracts being highly compatible for human consumption and capable for being used for the treatments, relief and remedy of respiratory problem.

Yet another objective of the present invention is to examine each of the extracts obtained from *M.koenigii* and *P. betel* leaves or their other plants parts individually and in combination on the inhibitory activity of 5-lipoxygenase-mediated Arachidonic acid oxidation and inducing the shift of Th2 type response towards Th1 type.

Yet another objective of the present invention is to assay 5-lipoxygenase mediated Arachidonic acid oxidation in an ex vivo human whole blood system in the presence of *M. koenigii* and *P. betel* leaves extracts or their other plant part extracts individually and in combination.

Yet another objective of the present invention is to assay the 5-lipoxygenase mediated Arachidonic acid oxidation in an ex vivo system with enriched human polymorphonuclear neutrophils (PMN) in the presence of *M. koenigii* and *P. betel* leaves extracts or their other plant part extracts, individually and in combination.

Yet another objective of the present invention is to analyze the production of intercellular cytokines by flow cytometry.

Yet another objective of the present invention is to provide intracellular IFN-gama and IL-4 profile as known markers for Th1 and Th2 type response respectively in ex vivo human whole blood with the extracts from *M. koenigii* and *P. betel* leaves individually and in combination

SUMMARY OF THE INVENTION

In accordance the present invention provides an herbal formulation useful for blocking of 5 lipoxygenase activity leading to the inhibition of leukotrine synthesis, suppression of IL4 production and enhancement of IFN gamma release Also, the present invention provides an herbal formulation for the treatment and remedy of bronchial respiratory difficulties. More particularly this invention provides a process for the preparation of extracts from the leaves or any other plant parts or seeds of plants *M. koenigii* and *P. betel* and their selective blending to evaluate biological response in order to establish their role for the treatment and remedy of bronchial respiratory troubles.

DETAILED DESCRIPTION OF THE INVENTION

The present invention also provides a herbal formulation useful for blocking of 5 lipoxygenase activity leading to the inhibition of leukotrine synthesis, suppression of IL4 production and enhancement of IFN gamma release. Also, the present invention provides a method of treating a subject for bronchial respiratory conditions, said method comprising administering to the subject effective amount of extracts obtained from the leafs or any other plant parts of *Piper betel* and *Murrya koenigii* or lyophilized extracts of *Piper betel* (PB) and *Murrya koenigii* (M.K) or a formulation comprising lyophilized extracts.

Accordingly, the present invention provides a pharmaceutical formulation useful as leukotrine and IL-4 synthesis inhibitor and Th1 type immunomodulator, said formulation comprising effective amount of extract or lyophilised extract obtained from the leaves or any other plant parts of *Piper betel* (PB) and *Muriva koenigii* (M.K) associated with or in combination with pharmaceutically acceptable additives.

In an embodiment of the present invention, the extract obtained from *Piper betel* is used as Th1 type immunomodulator and the extract obtained from *Murrya koenigii* (M.K) is used for leukotrine synthesis inhibitor.

In another embodiment of the invention provides a the formulation comprising effective amount of lyophilized extracts of *P.betel* and *M.koenigii* optionally associated with or in combination with a pharmaceutically acceptable carrier wherein, the carrier is selected in such a manner it does not interfere with the activity of lyophilized extracts of piper betel and *M. koenigii* extracts In another embodiment of the invention relates to the selection of additive. The additive is selected from nutrients such as proteins, carbohydrates, sugar, talc, magnesium stearate, cellulose, calcium carbonate, starch-gelatin paste and/or pharmaceutically acceptable carriers, excipient, diluent or solvent.

Still another embodiment, the aqueous extract, lyophilized product or the formulation is administered inhalation, oral, intravenous, intramuscular, subcutaneous route or any other suitable routes and the oral route is in the form of capsule, syrup, concentrate, powder or granules.

Still another embodiment relates to the amount of aqueous extract, lyophilized product or the formulation is administered by intravenous route is less than the oral route.

In yet another embodiment, the ratio of betel extract to the M.K extract is in the range between 1:1.0 to 1:5.0.

In yet another embodiment, the proportion of M.K extract or lyophilized extract is equal to or greater than the amount of betel extract or lyophilised to the M.K extract.

In yet another embodiment, the formulation comprising the betel extract and M.K extract is administered at a dosage level between 1 to 20 mg/kg of body weight up to three times a day for a period at least 4 weeks.

In yet another embodiment, the formulation comprising the betel extract and M.K extract is administered for a period of at least 4 weeks and up to three months depending upon the conditions.

In yet another embodiment relates to a method for treating animals and human beings.

One more embodiment relates to a pharmaceutical formulation useful for the treatment of bronchial respiratory conditions, said formulation comprising effective amount of lyophilized extracts obtained from the leafs or any other plant parts of *Piper betel* (PB) and *Murrya koenigii* M.K) optionally associated with or in combination with pharmaceutically acceptable additive.

Another embodiment of the present invention, the plant parts used for preparing the extracts or lyophilized extracts is selected from leafs, stems, barks, fruits, seeds or any other parts of the plants *Piper betel* (PB) and *Murrya koenigii* (M.K)

In one more embodiment relates to the use of formulation for shifting Th2 type response to Th1 type response.

Yet another embodiment relates to the use of formulation for inhibiting 5-lipooxygenase mediated Arachidonic acid oxidation in neutrophils enriched fraction of whole blood.

Yet another embodiment relates to the use of formulation for enhancing IFN-gamma and reducing IL-4 response in ex-vivo human whole blood.

Yet another embodiment relates to the use of formulation for enhancing IFN-gamma response in ex vivo human whole blood mononuclear (PMN)

Yet another embodiment relates to the use of formulation for reducing IL-4 response in human peripheral whole blood mononuclear cells.

In another embodiment relates to use of piper betel leaf extract and M.K leaf extract or extract obtained from any other plant parts of plants *Piper betel* and M.K for the treatment of bronchial respiratory conditions.

Yet another embodiment relates to use of betel leaf extract and M.K leaf extract or extract obtained from any other plant parts of plants *Piper betel* and M.K for shifting Th2 response to Th1 response.

Yet another embodiment relates to use of betel leaf extract and M.K leaf extract or extract obtained from any other plant parts of plants *Piper betel* and M.K for inhibiting 5-lipooxygenase mediated Arachidonic acid oxidation in neutrophils enriched fraction of whole blood.

Yet another embodiment relates to use of betel leaf extract and M.K leaf extract or extract obtained from any other plant parts of plants *Piper betel* and M.K for enhance IFN-gamma and reduce IL-4 response in ex vivo human whole blood.

Yet another embodiment relates to use of betel leaf extract and M.K leaf extract or extract obtained from any other plant parts of plants *Piper betel* and M.K for enhance IFN-gamma response in ex vivo human whole blood mononuclear (PMN)

Yet another embodiment relates to use of betel leaf extract and M.K leaf extract or extract obtained from any other plant parts of plants *Piper betel* and M.K for reducing IL-4 response in human peripheral whole blood mononuclear cells.

In an embodiment of the present invention, the extracts obtained from the plants *M. koenigii* and *P. betel* are mixed with freshly drawn human blood.

In an another embodiment of the present invention, the cells in an ex vivo human blood system activated with calcium inophor or the likes.

In an another embodiment of the present invention, extracts from *M. koenigii* and *P. betel* leaf are blended by the technique known in the art.

In an another embodiment of the present invention, the leaf extracts are made from fresh or sun/shade dried of *M. koenigii* and *P. betel.*

In an another embodiment of the present invention, plant material are used for extraction with appropriate solvent such as methanol or water or buffer in a percolator or the equipment known in the art.

In an another embodiment of the present invention, the extracts of *M. koenigii* and *P. betel* are concentrated under reduced pressure to save active principle.

In yet another embodiment of the present invention, the concentrates are lyophilised to remove reduced water and other residual solvent.

In yet another embodiment of the present invention, the fraction found active as inhibitor of 5-lipoxygenase mediated Arachidonic acid oxidation in an ex vivo whole human blood are selected for formulation.

In yet another embodiment of the present invention, the extracts of *M. koenigii* and *P. betel* found active for shifting from Th2 type response to the Th1 response are selected for formulation.

In yet another embodiment of the present invention, the extracts of *M. koenigii* and *P. betel* inhibited 5-lipoxygenase mediated Arachidonic acid oxidation in neutrophils enriched fraction of whole blood.

In yet another embodiment of the present invention, the blended extract of *M. koenigii* and *P. betel* is found to enhance IFN-gama and reduce IL-4 response in ex vivo human whole blood.

In yet another embodiment of the present invention, the extract obtained from *P. betel* is found to enhance IFN-gama response in ex vivo human blood mononuclear (PMN).

In yet another embodiment of the present invention, the formulated extract prepared from the leaf extracts of *M. konigii* and *P. betel* is found to reduce IL-4 response in human peripheral blood mononuclear cells.

In yet another embodiment of the present invention, the leaf extracts of *M. konigii* and *P. betel* were found as inhibitors of 5-lipoxygenase mediated arachidonic acid oxidation assayed after incubation of whole blood and lysing the cells at the time of assay were chosen for formulation.

DESCRIPTION OF FIGURES

FIG. 1 describes the flow cytometric determination of intracellular IFN-gamma and IL-4 in ex vivo human mononuclear cells after co-culture with phytohemmaglutinin in the presence or absence of extracts obtained from *M. Koenigii* and *P. betel*. Our data indicate that the extract from *P. betel* increased IFN-gamma positive cells and reduced IL-4 positive cells markedly. *M. koenigii* extract had reduced IL-4 positive as well as IFN-gamma positive cells. Combination of these two extracts increased IFN-gamma positive cells to the control level and still maintained reduced level of IL-4 positiity

EXAMPLE-1

Collection of Plant Material

The leaves of *Murraya Koenigii* and *Piper betel* were collected from shrubs and climber respectively from different areas of West Bengal, India. A voucher specimen is deposited at the department of Medicinal Chemistry at the Indian Institute of Chemical Biology, 4 Raja S.C. Mullick Road, Calcutta-700032.

EXAMPLE 2

Preparation of the Active Material

Fresh leave containing branches of *Murraya Koenigii* collected, cleaned and washed with water after getting from the local supplier and used as starting materials.

410 gm of the fresh leaves of *Murraya Koenigii* was made a paste in a mixture-blender in a methanol (1000 ml) and was placed in a glass percolator (5 lit. capacity) with the addition of 1000 ml of methanol. This was kept for 16 hrs (overnight) at room temperature. Filtering the extract through Whatman No. 1 filter paper collected the percolate. The process of extraction was repeated four times and the combined extract was evaporated to dryness under reduced pressure in a rotary evaporator, keeping the temperature at 40° C. (bath). The solid residual matter left was viscous in appearance and it was further dried by lyophilization. The yield was 25.63 gm. (MKOC)

150 gm of fresh leaves of $M$. $konigii$ thoroughly washed in sterile water was homogenized with 750 ml of glass distilled water in a mixture-blender and then sonicated in an ultrasonic bath with 5 burst each for 5 minutes. Filtering through Whatman no 1 filter paper separated the material extracted in water. This type of treatment for extracted was repeated for three times. The combines extract was byophilized yielding a powdered material (MKOC) 11 gm in weight.

The fresh leaves of $P$ $betle$ (1.5 kg homogenized with distilled water(500 ml)in a mixture-blender and then sonicated in an ultrasonic bath with 3 burst each for 15 min. It was allowed to be extracted overnight or 16 hrs. Filtering through Whatman No. 1 filter paper separated the material extracted in water. This type of treatment for extraction was repeated for three times. The combined extract was evaporated to dry in a flash evaporator under reduced pressure at 40° C. The residual substance was then dried in a desiccator under high vacuum and the semi-solid (14.92 gm) (JB01) was left.

3 gm extract of $M$. $koenigii$ and 3 gm extract of $P$. $betel$ were mixed together homogeneously with adding a few drops of water. The whole extract was evaporated to dryness in a freeze-drier. This extract was tested for biological activity (MKOC+JB01).

EXAMPLE-3

Fresh leaves of $M$. $koenigii$ (70 gm) and $P$. $betel$ (500 gm) were mixed together and was thoroughly washed with distilled water. It was homogenized with distilled water (300 ml) in a mixture-blender. It was then sonicated in an ultrasonic bath with 3 burst each for 15 min. The extract was filtered through Whatman No. 1 filter paper and the filtrate was collected. This process of extraction was repeated three times. The combined extract was lyophilized yielding a semi-solid mass (10 gm). This was then tested for biological activity (MKOc+JB01) Since the leaf of both the plants are widely used for making various food preparations in India, its biocompatibility and toxicity need not worry anyone. Further, both the plants are ubiquitous. The presence of the active factors in the leaf of $Murraya$ $koenigii$ and $Pipe$ $betel$ useful for relief, treatment and cure of respiratory problems has been demonstrated here and its preparation is fast, convenient and inexpensive. Feeding of leaves extract to animals did not produce any adverse effect.

EXAMPLE 4
Description of the Method for Measuring Inhibition of Arachidonic Acid Oxidation.

500 µl of heparinised human peripheral blood half diluted with PBS was taken in each well of a 24-well tissue culture plate. 10-µg/ml concentration of each extract sample was added in each well. The cells were then incubated for 3 hr. at 37° C. with occasional shaking. The 10 µl /ml of arachidonic acid solution (12.2 mg/ml of absolute alcohol stored under argon at −20° C.) was added to each well for 5 min prior to the addition of calcium ionophore (A23187) at a concentration of 20µ/ml to continue the incubation for further 10 min. Volume of the cell suspension was made up to 2 ml with PBS and its oxygen content was monitored with the help of a sensitive Oxygraph instrument.

EXAMPLE-5

500 µl of half diluted human peripheral blood was incubated with 10 µg/ml of each extract for 3 hr. at 37° C. with occasional shaking. Then 10 µl/ml of arachidonic acid solution (12.2 mg/ml of absolute alcohol stored under argon at −20 ° C.) was added to each well for 5 min prior to the addition of calcium ionophore (A23187) at a concentration of 20 µg/ml to continue the incubation for further 10 min. Volume of the cell suspension was made up to 2 ml by addition 1 ml of PBS+500 µl of water to lyse the cells. Oxygen content of the cell lysate was monitored in a sensitive Oxygraph instrument.

EXAMPLE-6

Heparinized human peripheral blood was mixed with equal volume of 2% gelatine solution in PBS and allowed to stand for half an hour when RBC were settled down at the bottom. Upper layer containing neutrophil enriched mononuclear cells was centrifuged and cell pellet was suspended in PBS. 500 µl of this cell suspension ($3 \times 10^6$ cells/well) was incubated with 10 µg/ml of each sample at 37° C. for 3 hrs. Then arachidonic acid solution 10 µl/ml (12.2 mg/ml) was added to each well for 5 min prior to the addition of calcium ionophore (A23187) at a concentration of 20 µg/ml to continue the incubation for further 10 min. Volume of the cell was made up to 2 ml with PBS and oxygen content of the cell suspension was monitored in a sensitive Oxygraph instrument.

Thus, extracts of $M$. $konigii$ and $P$. $betel$, have been screened for biological activity relevant to the relief, treatment and cure of respiratory problems, and the processed extract, have been analysed by Thin Layer chromatography and HTPLC. The blended extract was dissolved and suspended finely in appropriate solvents and used in the test system (ex vivo whole human blood to establish the stipulated biological response.

EXAMPLE-7
Preparation of Intracellular Interferon Gamma (IFN-γ) and Interleukin-4 (IL-4) by Flow Cytometry Heparinized whole blood (0.1 ml/ well of 24 well plates, collected from normal individuals ) were cultured at 37° C. in 5% $CO_2$ for 6 hours in a total volume of 1.0 ml Rosewell Park Memorial Institute (RPMI) medium containing 10% heat inactivated fetal bovine serum and phytohaemaglutinin( PHA, 10 µg/ml) in the presence or absence of $P.betel$ and $M.koenigii$ leaves extract (1.0 mg/ml each) either alone or in combination. To cause the intracellular accumulation of newly synthesized proteins, brefeldin A (10 µg/ml ) was added to the cells for last 4 hours. At the end of incubation period, cells were treated with FACS™ lysing solution (Becton Dickinson, USA) for lysis of RBC. Cells were then washed, permeabilized by treatment with 4% paraformaldehyde for 10 minutes. After washing with washing buffer (phosphate buffered saline [PBS] containing 1% albumin, 0.1% saponin and 0.1% Sodium azide), permeabilized cells were treated with either FITC-labeled anti-IFN γ monoclonal antibody or PE-labeled anti-IL-4 monoclonal antibody for 20 minutes in room temperature at dark. Cells were washed with washing buffer and then resuspended in PBS containing 1% paraformaldehyde for single colour flow cytometry analysis using FACS Calibur (Becton Dickinson, USA) with the programme Cell Quest. Ten thousand cells were collected for each sample and the fluorescence intensity was measured on a logarithmic scale. To make sure that only intracellular IFN γ or IL-4 was being detected, cells were stained with FITC-labeled anti-IFN γ or PE-labeled anti-IL-4 antibody before permeabilization and gave less than 0.2% fluorescent cells for each staining. Irrelevant isotype-matched control antibody also produced only less than 0.1% fluorescent cells.

Flow cytometric determination of intracellular IFN-gamma and IL-4 in ex vivo human mononuclear cells after co-culture with phytohemmaglutinin in the presence or absence of extracts obtained from *M. Koenigii* and *P. betel*. Our data indicate that the extract from *P. betel* increased IFN-gamma positive cells and reduced IL-4 positive cells markedly. *M. koenigii* extract had reduced IL-4 positive as well as IFN-gamma positive cells. Combination of these two extracts increased IFN-gamma positive cells to the control level and still maintained reduced level of IL-4 positive.

RESULTS OF EXAMPLE -4

| Components | % inhibition of $O_2$ consumption |
|---|---|
| None | — |
| MK0C | 81.1 |
| JB01 | 3 |
| MK0C + JB01 | 77.73 |

RESULTS—EXAMPLE-5

| Components | % inhibition of $O_2$ consumption |
|---|---|
| None | — |
| MK0C | 89.62 |
| JB01 | 5.42 |
| MK0C + JB01 | 83.20 |

RESULTS OF EXAMPLE-6

| Components | % inhibition of $O_2$ consumption |
|---|---|
| None | — |
| MK0C | 88.76 |
| JB01 | 4.58 |
| MK0C + JB01 | 85.94 |

EXAMPLE 8

Results of Therapeutic Evaluation of the Preparation Developed by Combination of *M koenigii* Bark and *P. betel* Leaves Extract for the Treatment of Respiratory Trouble. (Conducted by a Registered Auyrvedic Practitioner Patient Sex Age Nature of respiratory Duration of disease Treatment period Improvement

| Patient | Sex | Age | Nature of respiratory | Duration of disease | Treatment period | Improvement |
|---|---|---|---|---|---|---|
| A | M | 46 | Recurrent wheezing Difficult breathing at night time, Chest tightness, Cough worsening at night. Domestic dust allergy and breathing problem. Allergic to fur/smoking | 27 years | 8 weeks | 90% All the inhaleer (6 puffs) were withdrawn |
| B | M | 39 | Recurrent wheezing Occasional chest tightness Difficult in breathing problem, | 14 years | 8 week | 80% No breathing problem except residual shortening occasionally |
| C | M | 62 | Recurrent wheezing Difficult breathing at night time. Allergy to dust causing breathing problem. Occasional chest tightness. Exercise induced breathing difficulties. | 50 year | 7 weeks | 70% No wheezing, No Exercise induced breathing difficulties No chest tightness |
| D | F | 28 | Cough, worse particularly At night, recurrent wheeze Recurrent difficult breathing. Recurrent chest tightness. Viral infection. Allargy to domestic dust mites. Changes in temperature | 20 year | 8 weeks | 90% No inhaler is Currently require No other drug is necessary |
| E | M | 87 | Cough, worse particularly At night, recurrent wheeze Recurrent difficult breathing. Recurrent chest tightness. Viral infection. Allargy to domestic dust mites. Changes in temperature | 30 year | 8 weeks | 90% No inhaler is Currently require No other drug is necessary, the bed ridden patient is moving on wheel chair without assistance. |

What is claimed is:

1. A pharmaceutical formulation useful as a leukotrine and IL4 synthesis inhibitor and as a Th1 immunomodulator, said formulation comprising an effective amount to function as said inhibitor and immunomodulator of a combination of extracts or lyophilised extracts obtained from *Piper betel* and *Murrya Koenigii*.

2. A formulation as claimed in claim 1, further comprising one or more pharmaceutically acceptable additives.

3. A formulation as claimed in claim 2, wherein said extracts are obtained from plant parts selected from the group consisting of leaves, stems, bark, fruits, and seeds.

4. A formulation as claimed in claim 2, wherein said additive is selected in such a manner that it does not interfere with the activity of said extracts or lyophilized extracts of *Piper betel* and *Murrya koenigii*.

5. A formulation as claimed in claim 2, wherein said additive is selected from the group consisting of proteins, carbohydrates, sugar, talc, magnesium stearate, cellulose, calcium carbonate, and starch-gelatin paste.

6. A formulation as claimed in claim 1, which is in a form to be administered through an inhalation, oral, intravenous, intramuscular or subcutaneous route.

7. A formulation as claimed in claim 6, wherein said form for oral route is selected from the group consisting of capsule, syrup, concentrate, powder and granules.

8. A formulation as claimed in claim 1, wherein the amount of *Murrya koenigii* extract or lyophilized extract is equal to or greater than the amount of *Piper betel* extract or lyophilized extract.

9. A formulation as claimed in claim 1, wherein the ratio of said *Piper betel* extract or lyophilized extract to said *Murrya koenigii* extract or lyophilised extract is in the range 1:1 to 1:5.

10. A method of treating an animal or human subject for bronchial respiratory conditions, said method comprising administering to the subject an effective amount to treat said conditions of a formulation as claimed in claim 1.

11. A method as claimed in claim 10, wherein said formulation further comprises a pharmaceutically acceptable additive.

12. A method as claimed in claim 11, wherein said additive is selected in such a manner that it does not interfere with the activity of said extract or lyophilised extract of *Piper betel* and *Murrya Koenigii*.

13. A method as claimed in claim 11, wherein said additive is selected from the group consisting of proteins, carbohydrates, sugar, talc, magnesium stearate, cellulose, calcium carbonate and starch-gelatin paste.

14. A method as claimed in claim 10, wherein said formulation is administered through an inhalation, oral, intravenous, intramuscular, or subcutaneous route.

15. A method as claimed in claim 14, wherein said form for oral route is selected from the group consisting of capsule, syrup, concentrate, powder and granules.

16. A method as claimed in claim 10, wherein the ratio of said *Piper betel* extract or lyophilized extract to said *Murrya Koenigii* extract or lyophilized extract is in the range 1:1 to 1:5.

17. A method as claimed in claim 10, wherein the proportion of *Murrya Koenigii* extract or lyophilised extract is equal to or greater than the amount of *Piper betel* extract or lyophilized extract.

18. A method as claimed in claim 10, wherein said formulation is administered at a dosage level between 1 to 20 mg/kg of body weight at least once a day for a period of at least 4 weeks depending upon the respiratory conditions.

19. A formulation as claimed in claim 1, further comprising a pharmaceutically acceptable carrier, excipient, diluent or solvent.

20. A method as claimed in claim 10, further comprising a pharmaceutically acceptable carrier, excipient, diluent or solvent.

\* \* \* \* \*